United States Patent
Buyuktimkin et al.

(10) Patent No.: US 9,833,488 B2
(45) Date of Patent: Dec. 5, 2017

(54) SENSITIZATION COMPOSITION AND METHOD OF USE

(71) Applicant: Centric Research Institute, Encinitas, CA (US)

(72) Inventors: Servet Buyuktimkin, San Diego, CA (US); Nadir Buyuktimkin, San Diego, CA (US); James L. Yeager, Lake Forest, IL (US); Albert Liu, Encinitas, CA (US)

(73) Assignee: Centric Research Institute, Encinitas, CA (US)

( * ) Notice: Subject to any disclaimer, the term of this patent is extended or adjusted under 35 U.S.C. 154(b) by 53 days.

(21) Appl. No.: 14/395,919

(22) PCT Filed: Mar. 15, 2013

(86) PCT No.: PCT/US2013/032371
§ 371 (c)(1),
(2) Date: Oct. 21, 2014

(87) PCT Pub. No.: WO2013/162769
PCT Pub. Date: Oct. 31, 2013

(65) Prior Publication Data
US 2015/0110904 A1    Apr. 23, 2015

Related U.S. Application Data

(60) Provisional application No. 61/638,106, filed on Apr. 25, 2012.

(51) Int. Cl.
| | |
|---|---|
| A61K 36/54 | (2006.01) |
| A61K 36/73 | (2006.01) |
| A61K 36/00 | (2006.01) |
| A61K 36/736 | (2006.01) |
| A61K 36/738 | (2006.01) |
| A61Q 19/00 | (2006.01) |
| A61K 8/92 | (2006.01) |
| A61K 9/00 | (2006.01) |
| A61K 9/107 | (2006.01) |
| A61K 36/23 | (2006.01) |
| A61K 36/53 | (2006.01) |

(52) U.S. Cl.
CPC ............ *A61K 36/738* (2013.01); *A61K 8/922* (2013.01); *A61K 9/0034* (2013.01); *A61K 9/107* (2013.01); *A61K 36/23* (2013.01); *A61K 36/53* (2013.01); *A61K 36/54* (2013.01); *A61K 36/736* (2013.01); *A61Q 19/005* (2013.01)

(58) Field of Classification Search
None
See application file for complete search history.

(56) References Cited

U.S. PATENT DOCUMENTS

| | | | | |
|---|---|---|---|---|
| 4,933,177 A | * | 6/1990 | Grollier | A61K 8/0212 |
| | | | | 106/31.03 |
| 5,605,651 A | * | 2/1997 | Balzer | A61K 8/062 |
| | | | | 424/401 |
| 2003/0039709 A1 | * | 2/2003 | Thrash | A61K 8/678 |
| | | | | 424/735 |
| 2009/0068128 A1 | * | 3/2009 | Waddington | A61K 8/673 |
| | | | | 424/59 |
| 2010/0215775 A1 | * | 8/2010 | Schmaus | A61K 8/23 |
| | | | | 424/685 |

FOREIGN PATENT DOCUMENTS

EP    0709084 A2 *    5/1996    ............. A61K 8/361

OTHER PUBLICATIONS

Cavanagh et al. (2002) Phytother. Res. 16, 301-308.*
Website document entitled: "Coriander Essential Oil: Uses, Benefits and Precautions" (available at http://www.sustainablebabysteps.com/coriander-essential-oil.html). Downloaded from website Jun. 16, 2016.*
Gediya et al. (2011) J. Nat. Prod. Plant Resour., 1(1): 24-32.*
Ghosh et al. (2013) Journal of Nanoscience and Nanotechnology, vol. 13, 114-122.*
Ramadan et al. (2003) J. Agric. Food Chem. 51: 6961-6969.*
Website document entitled: "What is the difference between sweet almond and bitter almond?" (available at http://www.susanssoaps.com/blog/what-is-the-difference-between-sweet-almond-and-bitter-almond?). Downloaded from website Jun. 16, 2016.*
Van Howe, Is Neonatal Circumcision Clinically Beneficial? Argument Against, Nat. Clin. Pract. Urol., 2009, pp. 74-75, vol. 6(2).

* cited by examiner

*Primary Examiner* — Chris R Tate
*Assistant Examiner* — Russell Fiebig
(74) *Attorney, Agent, or Firm* — Olson & Cepuritis, Ltd.

(57) ABSTRACT

The present invention relates to a topical composition and method of use, specifically an oil-in-water emulsion, comprised of sweet almond oil, lavender oil, rose oil, cinnamon bark oil, and coriander seed oil in a physiologically acceptable topical carrier. The composition is applied to a circumcised penis to enhance sensitivity, preferably twice daily for a time period of at least about two weeks. Thereafter a maintenance dose can be applied once a day to maintain a desired level of sensitivity.

4 Claims, No Drawings

SENSITIZATION COMPOSITION AND METHOD OF USE

CROSS-REFERENCE TO RELATED APPLICATION

This application is a U.S. National Stage of PCT/US2013/032371, filed Mar. 15, 2013 and claims the benefit of U.S. Provisional Application No. 61/638,106, filed on Apr. 25, 2012, each of which is incorporated herein by reference in its entirety.

FIELD OF THE INVENTION

This invention relates generally to a non-irritating topical composition for increasing the sensitivity of the penis during sexual activity. More specifically, the invention relates to an oil-in-water emulsion for application to a circumcised penis for enhanced sensitivity.

BACKGROUND OF THE INVENTION

An intact human penis is covered by a single continuous sheath or skin system which is partly folded at different times. The folded portion of the skin system is called the foreskin or prepuce. Historically, the foreskin has been delineated as a separate anatomical structure; however, this is not correct. The foreskin is not a separate anatomical structure from the rest of the skin of the penis but rather it is the portion of the continuous skin system which happens to be folded over the glans at any given time.

Circumcision is the surgical procedure by which the foreskin is removed. Many cultures perform circumcision on infant males soon after birth; however, the procedure is also sometimes performed on adult males. Male circumcision is performed for a variety of reasons; religious, health, aesthetic, tradition, etc. Recent studies have brought into question some of the justifications for circumcision inasmuch as circumcision removes a complex, pentilaminar functional structure that contains nearly all fine touch neuroceptors of the penis and can reduce sensitivity of the glans penis to fine touch and vibration. Van Howe, Nat. Clin. Pract. Urol. 6(2):74-75 (2009).

SUMMARY OF THE INVENTION

A composition for topical application to a circumcised penis to enhance sensitivity comprises an admixture of sweet almond oil, lavender oil, cinnamon bark oil, coriander seed oil and rose oil in a physiologically acceptable topical cream, i.e, an oil-in-water emulsion having the consistency of a viscous liquid or semi-solid.

DETAILED DESCRIPTION OF PREFERRED EMBODIMENTS

The composition of the present invention is an oil-in-water emulsion comprising sweet almond oil, lavender oil, cinnamon bark oil, coriander seed oil and rose oil, preferably in a respective weight proportion of about 200:33:25:17:1. The oil-in-water emulsion is a viscous liquid or semi-solid having a cream-like consistency. The preferred dosage amount is approximately 150-300 mg of the composition per dose.

Table 1 lists the components of the composition in recommended weight percent ranges, as well as the preferred weight percent.

TABLE 1

| Component | wt % | pfd wt % |
|---|---|---|
| sweet almond oil[1] | 2-10 | 6 |
| lavender oil[2] | 0.01-2 | 1 |
| rose oil[3] | 0.005-1 | 0.03 |
| cinnamon bark oil[4] | 0.01-2 | 0.75 |
| coriander seed oil[5] | 0.01-1 | 0.5 |
| sorbitol | 0.7-7 | 3.5 |
| isopropyl alcohol | 0-7 | 2.8 |
| propylene glycol | 5-25 | 20 |
| butylated hydroxytoluene | 0.01-2 | 1 |
| triethanolamine | 0.05-3 | 1 |
| benzyl alcohol | 0.01-3 | 1 |
| benzyl benzoate | 0.01-5 | 1 |
| PEG 40-hydrogenated castor oil[6] | 1-5 | 3.5 |
| acrylate/C10-30 alkyl acrylate crosspolymer[7] | 0.25-4 | 1.3 |
| disodium EDTA | 0.01-0.2 | 0.1 |
| water | q.s. to 100% | q.s. to 100% |

[1] *Prunus Amygdalus Dulcis* oil
[2] *Lavandula Angustifolia* oil
[3] *Rosa Damascena* oil
[4] *Cinnamomun Zeylanicum* bark oil
[5] *Coriandrum Sativum* seed oil
[6] Cremophor RH40
[7] Pemulen TR1

The present compositions can be prepared in a batch process as described below.

An aqueous dispersion is prepared using about 90 weight percent of required water, to which are added the acrylate crosspolymer and disodium ethylene diamine tetraacetic acid (EDTA). The resulting admixture is stirred until a substantially complete dispersion is achieved usually for about two hours. A 70 weight percent solution of sorbitol in water is then added with stirring, and the stirring is continued until a substantially homogeneous composition is obtained.

A separate homogenous dispersion is prepared by admixing PEG 40-hydrogenated castor oil, benzyl alcohol, benzyl benzoate butylated hydroxytoluene, isopropanol and propylene glycol.

The prepared dispersions are then quantitatively combined in a single vessel with stirring and the mixture of sweet almond oil, lavender oil, cinnamon bark oil, coriander seed oil and rose oil is added to the combined dispersions with stirring until a homogenous dispersion is produced. The stirring is continued for at least about one hour.

A solution of triethanolamine in the remaining ten weight percent of water is then slowly added to the produced homogenous dispersion with stirring which is continued for at least 30 minutes to produce a smooth, cream-like composition.

EXAMPLE

A cream prepared in the foregoing manner and containing the preferred amount of constituents shown in Table 1 was administered to eight circumcised male patients (age: 28 to 65 years). A dose of about 150 milligrams was applied to the glans penis twice a day for a two week period.

Six of the eight patients reported that they experienced a lasting increased sensitivity of the glans penis after the two-week treatment period.

A preferred method of use comprises application of the composition to the glans penis twice daily for at least about two weeks, preferably in an amount in the range of about 150 to about 300 milligrams per application. Thereafter a maintenance dose can be applied once a day to maintain a desired level of sensitivity.

The foregoing description and the example are intended as illustrative and are not to be taken as limiting. Still other variants within the spirit and scope of the present invention are possible and will readily present themselves to those skilled in the art.

We claim:

1. A topical sensitization composition comprising an effective amount of an admixture of sweet almond oil, lavender oil, cinnamon bark oil, coriander seed oil and rose oil, wherein the oils are present in said admixture at a respective weight ratio of about 200:33:25:17:1; and
    wherein the composition is in the form of a physiologically acceptable oil-in-water emulsion.

2. The topical composition in accordance with claim 1 wherein the oil-in-water emulsion has the consistency of a topical cream.

3. A topical oil-in-water emulsion sensitization cream composition comprising, based on the weight of the composition:
    about 2 to about 10 weight percent sweet almond oil, about 0.01 to about 2 weight percent lavender oil, about 0.005 to about 1 weight percent of rose oil, about 0.01 to about 2 weight percent cinnamon bark oil, about 0.01 to about 1 weight percent of coriander seed oil, about 0.7 to about 7 weight percent sorbitol, zero to about 7 weight percent isopropyl alcohol, about 5 to about 25 weight percent of propylene glycol, about 0.01 to about 2 weight percent butylated hydroxytoluene, about 0.05 to about 3 weight percent triethanolamine, about 0.01 to about 3 weight percent benzyl alcohol, about 0.01 to about 5 weight percent benzyl benzoate, about 1 to about 5 weight percent of polyethylene glycol (40)-hydrogenated castor oil, about 0.25 to about 4 weight percent acrylate/C10-30 alkyl acrylate crosspolymer, about 0.01 to about 0.2 weight percent disodium ethylene diamine tetraacetic acid, and the remainder water.

4. The topical composition of claim 3 and consisting essentially of, based on the weight of the composition:
    about 6 weight percent sweet almond oil, about 1 weight percent lavender oil, about 0.03 weight percent of rose oil, about 0.75 weight percent cinnamon bark oil, about 0.5 weight percent coriander seed oil, about 3.5 weight percent sorbitol, about 2.8 weight percent isopropyl alcohol, about 20 weight percent propylene glycol, about 1 weight percent butylated hydroxytoluene, about 1 weight percent triethanolamine, about 1 weight percent benzyl alcohol, about 1 weight percent benzyl benzoate, about 3.5 weight percent polyethylene glycol (40)-hydrogenated castor oil, about 1.3 weight percent acrylate/C10-30 alkyl acrylate crosspolymer, about 0.1 weight percent disodium ethylene diamine tetraacetic acid, and the remainder water.

* * * * *